United States Patent [19]
Mouchawar et al.

[11] Patent Number: 6,002,963
[45] Date of Patent: Dec. 14, 1999

[54] MULTI-AXIAL ACCELEROMETER-BASED SENSOR FOR AN IMPLANTABLE MEDICAL DEVICE AND METHOD OF MEASURING MOTION MEASUREMENTS THEREFOR

[75] Inventors: Gabriel Mouchawar, Newhall; James D. Causey, III, Simi Valley; Sheldon B. Moberg, Granada Hills, all of Calif.

[73] Assignee: Pacesetter, Inc.

[21] Appl. No.: 08/390,738

[22] Filed: Feb. 17, 1995

[51] Int. Cl.$^6$ ..................................................... A61N 1/36
[52] U.S. Cl. ................................................. 607/18; 607/19
[58] Field of Search ................................ 607/17, 18, 19, 607/21, 22, 24

[56] References Cited

U.S. PATENT DOCUMENTS

| | | | |
|---|---|---|---|
| 4,140,132 | 2/1979 | Dahl | 128/419 PG |
| 4,202,339 | 5/1980 | Wirefeld et al. | 607/22 |
| 4,305,396 | 12/1981 | Wittkampf et al. | 128/419 PG |
| 4,428,378 | 1/1984 | Anderson et al. | 128/419 PG |
| 4,686,988 | 8/1987 | Sholder | 128/419 PG |
| 4,712,555 | 12/1987 | Thornander et al. | 128/419 PG |
| 4,791,931 | 12/1988 | Slate | 128/419 PG |
| 4,813,421 | 3/1989 | Baudino et al. | 607/22 |
| 5,014,700 | 5/1991 | Alt | 128/419 PG |
| 5,031,615 | 7/1991 | Alt | 128/419 PG |
| 5,040,534 | 8/1991 | Mann et al. | 128/419 PG |
| 5,040,535 | 8/1991 | Mann et al. | 128/419 PG |
| 5,044,366 | 9/1991 | Alt | 128/419 PG |
| 5,318,596 | 6/1994 | Barreras et al. | 607/19 |
| 5,330,510 | 7/1994 | Legay et al. | 607/19 |
| 5,423,869 | 6/1995 | Poore et al. | 607/18 |
| 5,626,622 | 5/1997 | Cooper | 607/18 |

OTHER PUBLICATIONS

Atochem Sensors, Inc. Product Brochure, *Standard and Custom Piezo Film Components*, pp. 1–10 (1991).

Bacharach, David W. et al., "Activity–Base Pacing: Comparison of a Device Using an Accelerometer Versus a Piezoelectric Crystal," *PACE*, vol. 15, pp. 188–196 (Feb. 1992).

Piezo Electric Products, Inc., "Piezoceramic Design Notes," *SENSORS* (Mar. 1984).

Salerno, David M. et al., "Seismocardiography: A New Technique for Recording Cardiac Vibrations. Concept, Method, and Initial Observations," *Journal of Cardiovascular Technology*, vol. 9, No. 2, 1990, pp. 111–118.

Salerno, David M. et al., Seismocardiography for Monitoring Changes in Left Ventricular Function During Ischemia. *Chest*, vol. 100, pp. 991–993 (Oct. 1991).

Salerno, David H. et al., "Seismocardiographic Changes Associated With Obstruction of Coronary Blood Flow During Balloon Angioplasty", *The American Journal of Cardiology*, vol. 68, pp. 201–207 (Jul. 15, 1991).

Sandler, H. et al., "Miniature Implantable Accelerometers," pp. 165–174.

*Primary Examiner*—William E. Kamm

[57] ABSTRACT

An improved sensor and related method for multi-axial measurement of motion for an implantable medical device is disclosed. The sensor has a wide variety of applications, including use as a cardiac wall motion sensor or a physical activity sensor. The sensor includes first and second conductors over which the motion measurements are made. A first transducer provides a first motion measurement indicative of sensor acceleration during a first phase, while a second transducer provides a second motion measurement indicative of sensor acceleration during a second phase. The first and second transducers are connected in parallel so as to provide the first and second motion measurements to an implantable medical device over the first and second conductors. The first and second phases are non-overlapping periods of time so that the motion measurements from each transducer are time division multiplexed. The sensor provides motion measurements that may either be compensated or uncompensated for temperature effects. In either case, the motion sensor uses fewer conductors than conventional sensors to deliver its measurements.

26 Claims, 4 Drawing Sheets

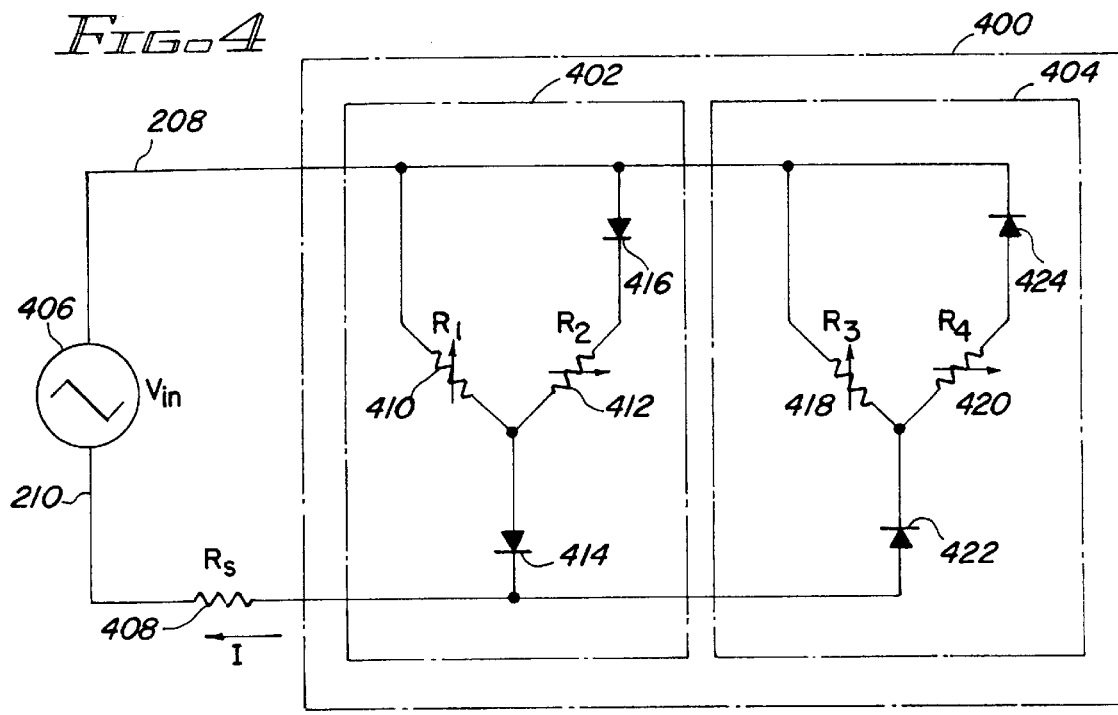
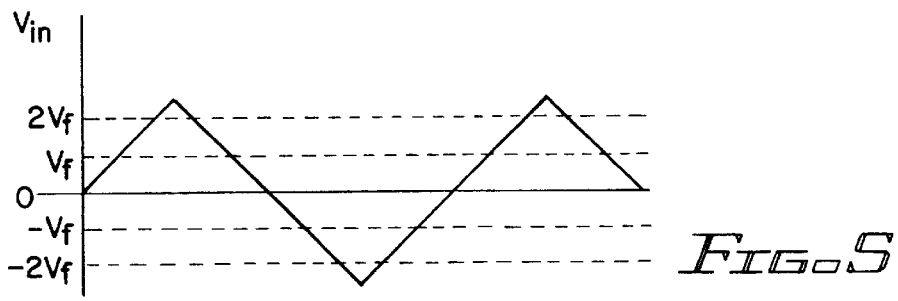
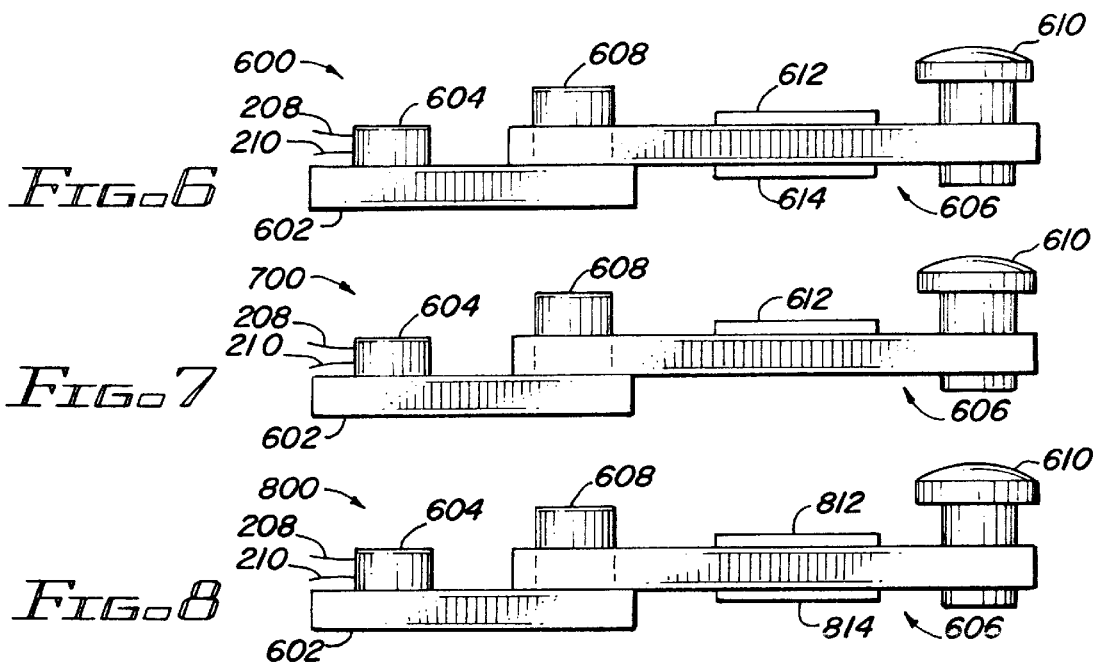

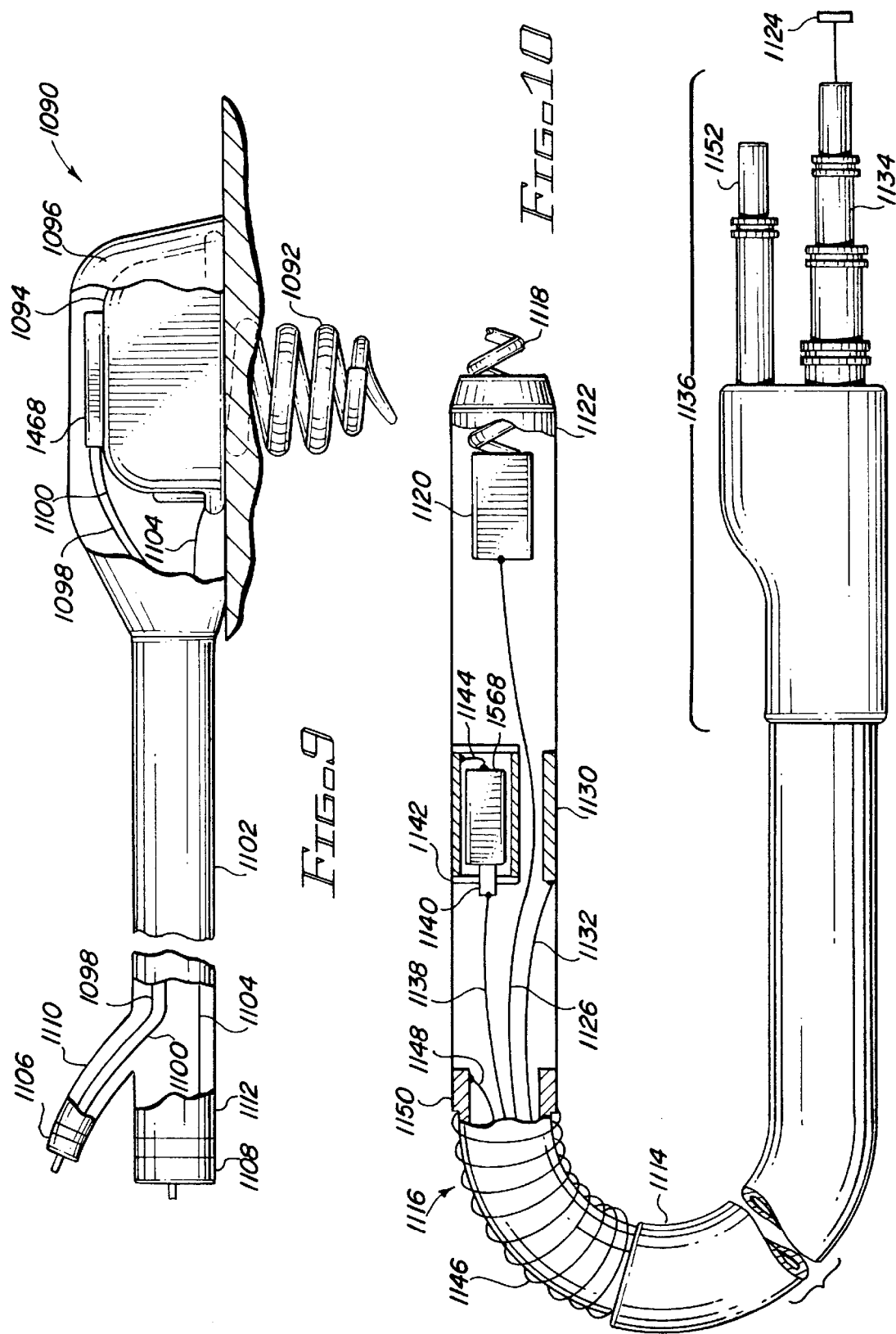

MULTI-AXIAL ACCELEROMETER-BASED SENSOR FOR AN IMPLANTABLE MEDICAL DEVICE AND METHOD OF MEASURING MOTION MEASUREMENTS THEREFOR

BACKGROUND OF THE INVENTION

This invention relates to implantable medical devices and more particularly to implantable cardiac stimulating devices and monitors. More particularly, this invention relates to sensor circuitry for such cardiac devices. The sensor circuitry can be configured to act as either a cardiac wall motion sensor to provide signals indicative of cardiac mechanical activity, or as a body sensor to measure overall physical activity.

Cardiac Wall Motion Sensors

One particular use of cardiac wall motion sensors is in the context of regulating cardiac stimulation. Implantable cardiac stimulating devices may be used to provide therapy in response to a variety of pathological cardiac arrhythmias. In particular, implantable cardiac stimulating devices may be capable of providing "tiered therapy," in which the type of electrical stimulation provided by the device is determined in accordance with the severity of the arrhythmia, with more aggressive therapies being applied in response to more severe arrhythmias. Thus, a cardiac stimulating device may respond to a relatively mild occurrence of tachycardia by delivering antitachycardia pacing pulses of approximately twenty-five to thirty microjoules in a sequence known to interrupt such an arrhythmia. In response to a relatively more severe occurrence of tachycardia, the device may deliver a low energy shock on the order of approximately two to five joules, either in combination with, or as an alternative to, antitachycardia pacing pulses. In response to an occurrence of an even more severe arrhythmia (ventricular fibrillation for example), the implantable cardiac stimulating device may deliver a high energy "defibrillation" shock on the order of approximately ten to forty joules.

Implantable cardiac stimulating devices are also employed to provide pacing pulses to cardiac tissue for the purpose of maintaining a heart rate at a physiologically acceptable rate (i.e., to provide "bradycardia pacing support"). Bradycardia pacing support may be provided by a dedicated pacemaker, or by a device that is also capable of providing other forms of therapy, such as tiered therapy.

Effective delivery of therapy from an implantable cardiac stimulating device depends upon accurate measurement of intrinsic cardiac activity. In the case of an implantable cardiac stimulating device capable of providing tiered therapy, the device must not only be capable of detecting the onset of an arrhythmia, but must also be capable of discriminating among various types of arrhythmias in order to deliver an appropriate form of electrical stimulation therapy. For example, if ventricular fibrillation is incorrectly diagnosed by the device as a relatively less severe arrhythmia, valuable time may be lost if an inappropriate, less aggressive therapy, such as antitachycardia pacing, is applied. Conversely, if tachycardia is incorrectly diagnosed as ventricular fibrillation, the patient may consciously experience high energy defibrillation shocks, which, although effective in terminating the tachycardia, are extremely uncomfortable, and may cause unnecessary myocardial stunning due to the defibrillation shock.

Measurement of intrinsic cardiac activity is also desirable for implantable cardiac stimulating devices (so-called "demand pacemakers") capable of providing bradycardia pacing support. Typically, the delivery of bradycardia pacing pulses from such devices is inhibited in response to spontaneous cardiac depolarizations (R-waves) which occur within a predetermined time period (commonly referred to as the "escape interval") following a preceding depolarization (R-wave). For example, if the intrinsic heart rate of a patient during a particular time interval is greater than a programmed rate, delivery of pacing pulses may be inhibited during that time interval. Pacing pulses would be provided when the intrinsic heart rate falls below the programmed rate. Pacing pulse inhibition is safer because it avoids competitive pacing, and is desirable because it extends battery life by avoiding delivery of unnecessary stimulation pulses. In order for a device to be capable of inhibiting delivery of pacing pulses, it must be capable of detecting intrinsic cardiac activity.

Many implantable cardiac stimulating devices that detect and discriminate among cardiac arrhythmias monitor heart rate, which is usually accomplished by measuring cardiac electrical activity—i.e., the intracardiac electrogram (IEGM). The IEGM is typically sensed by electrodes that are also used to deliver electrical stimulation therapy to the cardiac tissue. However, under some circumstances, it is difficult to sense the IEGM. For example, the device may not be able to discern the IEGM over noise or other physiological electrical activity, or perhaps even external interference. As a result, an implantable cardiac stimulating device may have difficulty detecting the onset of an arrhythmia. As another illustration, implantable cardiac stimulating devices capable of providing bradycardia pacing support may be inhibited from sensing cardiac electrical activity during a period of time immediately following the delivery of a pacing pulse, due to the presence of a pulse-induced afterpotential.

Other known implantable cardiac stimulating devices use hemodynamic signals to detect cardiac arrhythmias. For example, U.S. Pat. No. 4,774,950 of Cohen refers to a system that may detect cardiac arrhythmias by measuring mean pressure at a variety of locations (e.g., mean arterial pressure, mean right ventricle pressure, mean left atrial pressure, mean left ventricle pressure or mean central venous pressure). For a selected mean pressure, a short term current mean pressure is compared to a long term mean baseline pressure, and if they differ by a predetermined value, the patient may be deemed to be experiencing a cardiac arrhythmia. The mean pressure data may also be used in combination with heart rate measurements to detect arrhythmias.

Another example of a device that uses hemodynamics to detect cardiac arrhythmias is described in U.S. Pat. No. 4,967,748 of Cohen. In that patent, blood oxygen level is measured at a particular site in the circulatory system of a patient. A comparison is made between a short term sensed blood oxygen level and a baseline blood oxygen level, and if they differ, the patient may be deemed to be experiencing a cardiac arrhythmia.

Unfortunately, the use of hemodynamic indicators such as mean pressure and blood oxygen level may have certain associated drawbacks. One possible drawback is that hemodynamic indicators may not respond rapidly to the onset of an arrhythmia. Thus, an implantable cardiac stimulating device that relies on such hemodynamic signals to detect cardiac arrhythmias may not deliver therapy as rapidly as desired.

One proposed solution which overcomes some of the drawbacks associated with the use of the IEGM and certain other hemodynamic indicators is described in commonly-assigned, copending U.S. patent application Ser. No. 08/091, 636, filed Jul. 14, 1993, now U.S. Pat. No. 5,628,777 of Moberg and Causey, entitled "Implantable Leads Incorporating Cardiac Wall Motion Sensors and Method of Fabrication and a System and Method For Detecting Cardiac Arrhythmias Using a Cardiac Wall Motion Sensor Signal," which is incorporated by reference herein in its entirety. That patent application describes cardiac wall motion sensors that provide signals indicative of cardiac mechanical activity. The sensors are incorporated into implantable leads, such as endocardial leads, myocardial active-fixation leads and epicardial patch electrodes. The sensors are accelerometer-based such that they provide signals representative of cardiac wall accelerations as experienced by the sensors in the leads.

As described in patent application Ser. No. 08/091,636 now U.S. Pat. No 5,628,777 of Moberg et al., signals from the therein-described cardiac wall motion sensor may be used to discriminate among various cardiac arrhythmias in a manner traditionally accomplished by analyzing electrocardiograms or aortic pressure signals. An implantable cardiac stimulating device may be constructed to receive both a cardiac wall motion sensor signal (which is indicative of cardiac mechanical activity) and an IEGM signal (which is indicative of cardiac electrical activity). The device may be configured to use either form of information, or both forms of information in combination, to detect and discriminate among various types of cardiac arrhythmias and to determine intrinsic heart rate. Moreover, as described in commonly-assigned, U.S. Pat. No. 5,480,412, issued Jan. 2, 1996 of Mouchawar et al., entitled "System and Method for Deriving Hemodynamic Signals from a Cardiac Wall Motion Sensor" (incorporated by reference herein in its entirety), cardiac wall displacement may be derived from the cardiac wall motion acceleration signal, and the displacement used as a hemodynamic indicator.

As described in U.S. patent application Ser. No. 08/091, 636, now U.S. Pat. No. 5,628,777 of Moberg et al., the cardiac wall motion sensor may be implemented as an accelerometer constructed of a cantilever beam having one end fixably coupled to a cardiac lead that is in contact with a cardiac wall surface. A mass is disposed on the other end of the cantilever beam, which is left free to move. As the cardiac wall moves, the resulting movement of the lead causes the beam to flex. The mass can be centered, i.e., symmetrically disposed about the free end, so that the beam flexes in response to motion perpendicular to the beam. Alternatively, the mass can be offset, i.e., asymmetric with respect to the planar surface of the beam, so that the beam will flex in response not only to motions perpendicular to the beam, but also coaxial with respect to the beam. The measured acceleration of the beam provides an indication of cardiac mechanical activity.

A piezoelectric material may be disposed on both surfaces of the beam. The surfaces of the piezoelectric material are polarized to bear an electric charge. In response to upward and downward deflections of the beam, the charge on the piezoelectric surfaces change in magnitude and polarity, and thereby provide a signal indicative of the accelerations of the cardiac wall to which the lead is attached. In the offset mass configuration, the signals represent motion in both the perpendicular and coaxial directions combined.

The use of a piezoelectric material in a cardiac wall motion sensor exhibits a number of disadvantages. The piezoelectric accelerometer cannot measure a DC response (i.e., it cannot measure a constant acceleration). Further, the piezoelectric material is subject to thermal drift. As the ambient temperature of the sensor changes with time, the electrical properties of the piezoelectric material change correspondingly.

To overcome these problems, the above-referenced application also describes the use of a piezoresistive material to coat both sides of the cantilever beam. A piezoresistive material undergoes a change in resistance when the material is subjected to a mechanical stress or strain. Preferably, each side of the cantilever is coated with piezoresistive deposits to eliminate the effects of temperature drift. When compensated in this manner, the piezoresistive accelerometer exhibits a DC response and thus can be used to measure constant acceleration.

One drawback of temperature-compensated sensors results from the bridge circuitry used to cancel out the temperature effects common to both the upper and lower piezoresistive surfaces of the beam. The bridge requires three wires for each cantilever beam to measure resistance. In contrast, an uncompensated sensor requires only two conductors to measure acceleration.

The number of conductors used to measure cardiac acceleration increases when motion sensitivity in more than one direction is desired. One cantilever beam bearing an offset mass is sensitive to the vector sum of cardiac wall motion in two directions. However, such a sensor does not provide separate measurements of acceleration in individual orthogonal directions. Unfortunately, the cumulative multi-axial measurement of a single-beam sensor may register a zero or reduced value because of cancellation of nonzero measurements in different directions. Thus, it may be desirable to obtain two or more distinct measurements of the amplitude of cardiac wall motion in at least two individual noncoaxial directions.

As described above, a cardiac wall motion sensor can measure uniaxial motion by employing a centered mass, rather than an offset mass, that is symmetric about the cantilever axis. The measurement of cardiac accelerations in two separate directions would then require two cantilevered sensors. Unfortunately such a configuration implementing the temperature-compensated piezoresistive bridge design would require five wires (three for each cantilever with one wire in common), thereby occupying valuable space in the implantable cardiac lead.

Physical Activity Sensors

Accelerometer-based sensors have also been used as body sensors to measure a patient's physiological activity. For example, a rate-responsive pacemaker uses such sensor measurements to control a patient's heart rate. Accelerometer-based physical activity sensors are described in commonly-assigned, U.S. Pat. No. 5,383,473, issued Jan. 24, 1995, entitled "A Rate-Responsive Implantable Stimulation Device Having a Miniature Hybrid-Mountable Accelerometer-Based Sensor and Method of Fabrication," of Moberg; and Ser. No. 08/091,850, filed Jul.14, 1993, now U.S. Pat. No. 5,425,750, entitled "Accelerometer-Based Multi-Axis Physical Activity Sensor for a Rate-Responsive Pacemaker and Method of Fabrication," of Moberg, both of which are incorporated by reference herein in their entirety.

The utilization of accelerometer-based sensors to measure physical activity is the result of an evolution in pacemaker design. Early demand pacemakers enabled a physician to adjust the heart rate to be maintained by telemetrically adjusting the length of the escape interval. However, this technique only allowed for adjustments to a fixed "programmed rate," and did not accommodate patients who required increased or decreased heart rates to meet changing physiological requirements during periods of elevated or reduced physical activity. Unlike a person with a properly functioning heart, these patients were paced so that a constant heart rate was maintained regardless of the level of the patient's physical activity. Consequently, during periods of elevated physical activity, these patients were subject to adverse physiological consequences, including lightheadedness and episodes of fainting, because their heart rates were forced by the pacemaker to remain constant.

Later pacemakers were capable of adjusting the rate at which pacing pulses are delivered in accordance with metabolic needs of the patient. These devices, known as "rate-responsive pacemakers," typically maintain a predetermined minimum heart rate when the patient is engaged in physical activity at or below a threshold level, and gradually increase the maintained heart rate in accordance with increases in physical activity until a maximum rate is reached. Rate-responsive pacemakers typically include circuitry that correlates measured physical activity to a desirable heart rate. In many rate-responsive pacemakers, the minimum heart rate, maximum heart rate, and the slope or curve between the minimum heart rate and the maximum heart rate are telemetrically programmable to meet the needs of a particular patient.

One approach that has been considered for correlating physical activity to an appropriate heart rate involves measuring a physiological parameter that reflects the level to which the patient is engaged in physical activity. Physiological parameters that have been considered include central venous blood temperature, blood pH level, QT time interval and respiration rate. However, certain drawbacks such as slow response time, excessive emotionally-induced variations, and wide variability across individuals, render the use of certain physiological parameters difficult. Accordingly, they have not been widely applied in practice.

More generally accepted have been rate-responsive pacemakers which employ sensors that transduce mechanical forces associated with physical activity. These sensors are similar to those used to measure cardiac wall motion. U.S. Pat. No. 4,140,132 (of Dahl) and U.S. Pat. No. 4,428,378 (of Anderson et al.) describe examples of rate-responsive pacemakers that maintain a paced heart rate in accordance with physical activity as measured by a piezoelectric sensor.

U.S. patent application Ser. No. 08/091,850, now U.S. Pat. No. 5,425,750 of Moberg, described above, also provides an accelerometer-based physical activity sensor that employs a weighted cantilever arrangement similar to that disclosed in commonly-assigned copending U.S. patent application Ser. No. 08/091,636, now U.S. Pat. No. 5,628,777 of Moberg et al. The physical activity sensor is preferably mounted within an implantable stimulation device so as to be responsive to bodily accelerations associated with physical activity. The sensor employs an offset-weighted cantilever arrangement to provide sensitivity to bodily accelerations that are both perpendicular and coaxial to the cantilever beam.

In the context of measuring physical activity, the multi-axial sensitivity of such a sensor overcomes the limitations on a physician's ability to choose only the common "front-back" axis of sensitivity for a particular patient, i.e., the axis that projects from the patient's chest (as described above with respect to U.S. Pat. No. 4,144,132 (Dahl)). However, a physician may decide that other axes of sensitivity are more appropriate for a particular patient, e.g., where a patient is frequently subjected, perhaps for occupational reasons, to externally induced forces in the vertical and/or lateral directions.

Moreover, it is difficult to position a single-axis physical activity sensor so as to orient it in a predetermined direction. Unfortunately, the sensor may be subject to "twirler's syndrome"—a condition in which the patient absentmindedly manipulates the pacemaker implanted beneath the skin, thereby changing its orientation from time to time. Changes to the axis of sensitivity may lead to unexpectedly high or low measurements of physical activity which can cause a pacemaker to make inappropriate heart rate adjustments.

The multi-axial sensor described in U.S. patent application Ser. No. 08/091,850, now U.S. Pat. No. 5,425,750 of Moberg suffers the same drawbacks of the offset-weighted cantilevered cardiac wall motion sensor described above. Like the cardiac wall motion sensor, a single-beam, offset-weighted physical activity sensor provides only a measurement of the vector sum of bodily accelerations in different directions. It does not provide individual measurements along each direction of movement, although it may be desirable for a physician to know whether the measured accelerations are taking place along a particular axis. Vertical motion may indicate that the patient is climbing a set of stairs, which would place a greater strain on the heart than a front-back walking motion. Thus, such information could be useful in providing the proper cardiac stimulation. However, to obtain the same temperature compensation advantages and individual directional measurements as desired in the cardiac wall motion sensor, the physical activity sensor described above would require the same number of measurement wires as the cardiac motion sensor for each sensor configuration.

For both cardiac wall motion sensors and physical activity sensors, one concern that must always be kept in mind when designing implantable cardiac monitors and stimulating devices is the need to conserve the limited space available within the implantable device and the associated leads. Both the size and the number of components required to construct physical activity sensors and cardiac wall motion sensors should thus be kept to a minimum. Any attempt to improve directional sensitivity should avoid the use of additional hardware components, including additional transducers or wires, to the greatest extent possible.

SUMMARY OF THE INVENTION

The present invention provides an improved sensor and related method for multi-axial measurement of motion for an implantable medical device. The sensor has a wide variety of applications, including use as a cardiac wall motion sensor or a physical activity sensor. The sensor of the present invention provides motion measurement that may either be compensated or uncompensated for temperature effects. In either case, the motion sensor of the present invention uses fewer conductors than conventional sensors to deliver its measurements.

The sensor includes first and second conductors over which the motion measurements are made. A first transducer provides a first motion measurement indicative of sensor acceleration during a first phase, while a second transducer provides a second motion measurement indicative of sensor acceleration during a second phase. The first and second transducers are connected in parallel so as to provide the first and second motion measurements to an implantable medical device over the first and second conductors. The first and second phases are non-overlapping periods of time so that the motion measurements from each transducer are time division multiplexed.

The sensor may be employed as a cardiac wall motion sensor and mounted in a lead of a cardiac monitoring or stimulating device. Alternatively, the sensor may be mounted to the implantable medical device itself to function as a physical activity sensor for a rate-responsive pacemaker.

The multiplexing function is performed as follows. Over the first and second conductors, the first and second transducers receive an excitation signal having a first polarity during the first phase and a second polarity opposite the first polarity during the second phase. In response to the excitation signal being in the first polarity, the first transducer conducts in a first direction while the second transducer does not conduct any current. Conversely, in response to the excitation signal being in the second polarity, the second transducer conducts in a second direction opposite the first direction, while the first transducer does not conduct. The first and second motion measurements are taken when the respective first and second transducers conduct current.

In one embodiment, each transducer includes a piezoresistive material in series with a diode. The diodes in the transducers are positioned to conduct in opposite directions during opposite phases when the excitation signal reaches a voltage level so as to forward bias one of the diodes. The first motion measurement is the resistance of the first piezoresistive material determined when the first transducer conducts, while the second motion measurement is the resistance of the second piezoresistive resistive material determined when the second transducer conducts.

In an alternative embodiment, each transducer is implemented as a piezoresistive half bridge. Diodes in the first transducer are positioned to conduct in a direction opposite to that of diodes in the second transducer. Each half bridge includes two piezoresistive elements and two diodes. Motion measurements are derived from measurements of the half bridge resistance each time a diode conducts.

The piezoresistive elements of either sensor of the present invention may be mounted on opposite sides of a cantilever beam having a fixed beam mount and a free end upon which is disposed a corresponding mass. The beam mount is affixed to a cardiac lead so as to respond to cardiac wall motion. Alternatively, the beam mount may be mounted to an implantable medical device to measure body motion. The piezoresistive material disposed upon the cantilever beam provides a beam measurement indicative of the acceleration experienced by the beam as it deflects when the corresponding mass is accelerated.

A first cantilever beam may be positioned with respect to a second cantilever beam so that corresponding beam measurements are respectively the first and second motion measurements and are indicative of sensor accelerations along a plurality of axes. If the beam mass on each axis is centered about the planar surface of the beam, and the first and second beam axes are orthogonal, then the first and second motion measurements are each indicative of acceleration along a distinct axis. If, however, the masses are offset with respect to the planar surfaces of the beams, then the first and second motion measurements, although each not indicative of acceleration along distinct axis, are together indicative of accelerations along three orthogonal axes.

The sensors of the present invention further accomplish temperature compensation. For the first sensor embodiment, the piezoresistive elements of the first and second transducers are each disposed on opposite sides of a single cantilever beam to provide a temperature-compensated motion measurement over the first and second conductors. For the second sensor embodiment, the first and second piezoresistive elements of each half bridge are disposed on opposite sides of a cantilever beam. Because this sensor includes two half bridges, it can provide temperature-compensated measurements over two conductors from not just one, but from two cantilever beams.

It should thus be appreciated that by multiplexing motion measurements, the sensors of the present invention can sense cardiac wall motion or physical activity using fewer wires than conventional sensors, thus conserving valuable space within the implantable medical device with which the sensors are used.

DESCRIPTION OF THE DRAWINGS

The objects, features and advantages of the present invention will be apparent to one skilled in the art in light of the following detailed description in which:

FIG. 4 illustrates an alternative circuit-level implementation of the multiplexed sensor of the present invention.

FIG. 5 is a graph of the excitation signal used by the embodiment of FIG. 4.

FIG. 6 illustrates an offset-weighted cantilever beam mount for the multiplexed motion sensor of the present invention.

FIG. 7 illustrates a non-temperature compensated, multi-axis cantilever beam mount for the multiplexed motion sensor of the present invention.

FIG. 8 illustrates a temperature compensated, multi-axis cantilever beam mount for the multiplexed motion sensor shown in FIG. 4.

FIG. 9 is a partial cutaway view of a preferred embodiment of a myocardial active-fixation lead incorporating a cardiac wall motion sensor in accordance with the principles of the present invention.

FIG. 10 is a partial cutaway view of a preferred embodiment of an endocardial lead incorporating a cardiac wall motion sensor in accordance with the principles of the present invention.

DETAILED DESCRIPTION OF THE INVENTION

The present invention provides a two-conductor accelerometer-based sensor for multi-axial measurement of motion for an implantable medical device. For purposes of explanation, specific details are set forth to provide a thorough understanding of the present invention. However, it will be apparent to one skilled in the art that the invention may be practiced without these details. In other instances, well known elements, devices, process steps and the like are not set forth in detail in order to avoid unnecessarily obscuring the invention.

Figure 1:
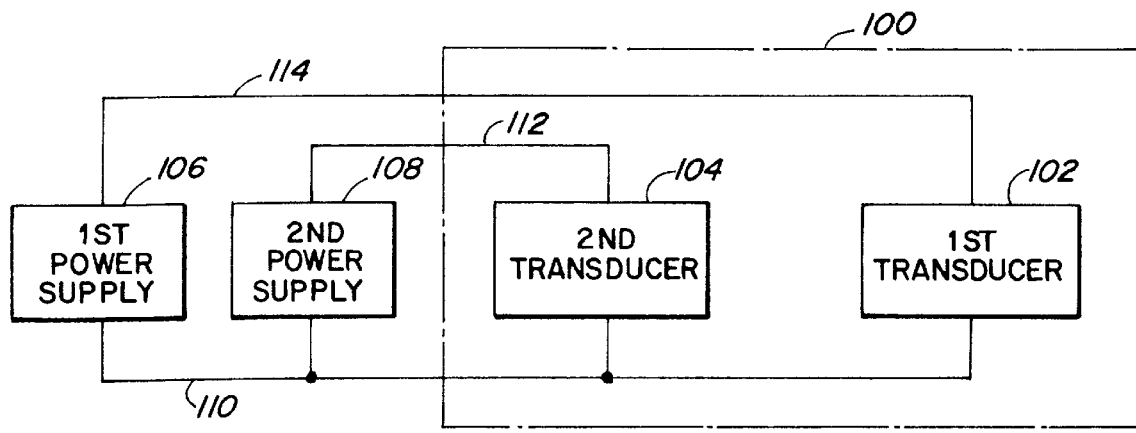
FIG. 1 is a system block diagram of an accelerometer-based motion sensor according to the prior art.

FIG. 1 illustrates a system block diagram of an accelerometer-based motion sensor 100 according to the prior art. The sensor 100 includes first and second transducing elements ("transducers") 102 and 104. The transducing elements 102 and 104 may be orthogonally mounted to measure accelerations in more than one direction, as described above. A first power supply 106 provides power to the transducing element 102, and a second power supply 108 provides power to the transducing element 104. Of course, the power from power supplies 106 and 108 may alternatively be provided by one power supply through a voltage divider. The accelerometer-based transducers 102 and 104 each emit a signal indicative of the acceleration experienced by the corresponding transducer. The signal emitted by the transducer 102 is measured over two wires 110 and 112, and the signals emitted by the transducer 104 are measured over a wire 114 and a common wire 110. Thus, it can be appreciated that the prior art sensor circuit 100 requires at least three output signal wires to obtain measurements from two transducers.

Figure 2:
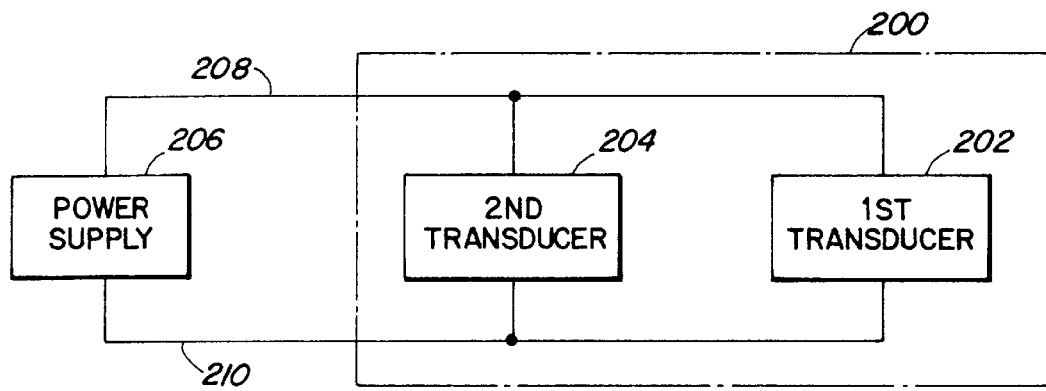
FIG. 2 is a system block diagram of a two-conductor, multiplexed accelerometer-based motion sensor of the present invention.

FIG. 2 illustrates a system block diagram of a two-conductor multiplexed accelerometer-based motion sensor 200 of the present invention. The sensor 200 includes a first transducing element 202 and a second transducing element 204. A single power supply 206 provides power to both transducing elements 202 and 204. Over two conductors 208 and 210, the transducers 202 and 204 provide first and second acceleration signals, respectively, that are indicative of the accelerations experienced by each transducer.

To ensure that each acceleration signal can be individually measured, the signals are time division multiplexed over the conductors 208 and 210. The multiplexing can be accomplished using synchronization circuitry (not shown) that alternately enables the first and second transducing elements 202 and 204 to output signals over the conductors 208 and 210. One skilled in the art would know how to implement the synchronization circuitry based upon this disclosure in light of the prior art. However, in the embodiments described below, the present invention avoids the need for such synchronization circuitry.

Figure 3:
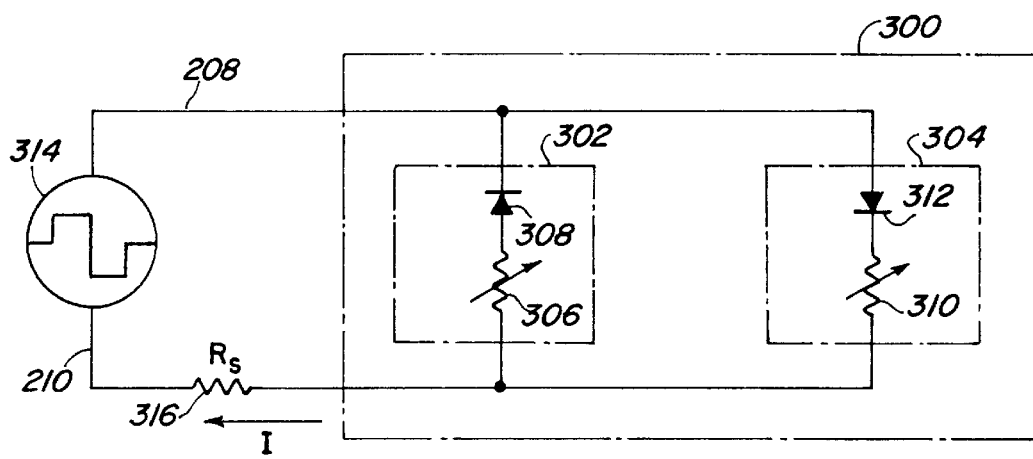
FIG. 3 illustrates one embodiment of a circuit-level implementation of the multiplexed sensor of the present invention.

FIG. 3 illustrates a circuit-level implementation of the multiplexed sensor of the present invention. A multiplexed sensor 300 includes two transducing elements 302 and 304. The first transducing element 302 is preferably constructed of a piezoresistive accelerometer 306 in series with a diode 308 that conducts in a first direction when forward biased. Similarly, the second transducing element 304 includes a second piezoresistive accelerometer 310 in series with a diode 312 that conducts in a direction opposite to that of diode 308 when forward biased. The diodes 308 and 312 are preferably implemented as Schottky diodes.

A power source 314 generates an AC signal for excitation of the transducing elements 302 and 304 over the two conductors 208 and 210. The excitation signal emitted by the power source 314 is preferably a square wave. The square wave must exhibit a voltage magnitude large enough to cause a voltage greater than the forward bias voltage of the diodes 308 and 312 to appeal across those diodes. In this configuration, only one of the diodes 308 and 312 is forward biased (turned on) during each phase of the excitation signal. Thus, only one accelerometer 306 or 310 will conduct current during each phase.

The current can be measured through a current sensing resistor $R_s$ 316 as shown in FIG. 3. The current sensing resistor $R_s$ has a negligible resistance on the order of 1–10 ohms. The resistance values of the transducers 302 and 304 can be independently measured during each phase by dividing the voltage of the excitation signal by the current flowing through the transducing element and subtracting the resistance of the current sensing resistor 316. Because of the negligible resistance of $R_s$ 316, the subtraction step can be omitted without significantly affecting the measurement of the transducer resistance, which is preferably on the order of 100–1000 ohms using current technology. Of course, the present invention may be implemented with transducers exhibiting a wide range of resistance values.

From these transducer resistance values, the acceleration experienced by each transducer can then be derived using conventional techniques. Because only one transducer conducts during each phase, the resistance values can be calculated from signals measured over only two wires, a distinct improvement over the prior art. As would be clear to one skilled in the art, the power source 314 and the circuitry (not shown) used to measure the resistances from the two conductors (and calculate the accelerations therefrom) preferably reside in the implantable medical device.

Piezoresistive materials experience noticeable variations in resistance as a function of temperature. In the human body, changes in the level of physical activity cause changes in the ambient temperature experienced by an implantable medical device. To provide temperature compensation, the piezoresistive accelerometers 306 and 310 are mounted in a sensor such that accelerations have opposite effects on their resistance, e.g., a positive acceleration should increase the resistance of the first accelerometer 306 and decrease the resistance of the second accelerometer 310. The acceleration value is then proportional to the difference of the resistance values. Because temperature will have the same effect on both resistances, the temperature effects are canceled by subtracting the resistance values.

FIG. 4 illustrates an alternative embodiment of the present invention. A multiplexed sensor 400 includes two transducing elements 402 and 404, which receive an excitation signal from a power source 406. The transducers receive the excitation signal through the two conductors 208 and 210 in series with a current sensing resistor $R_s$ 408. As in the previous embodiment the value of $R_s$ 408 is negligible, on the order of 1–10 ohms. Each transducing element is constructed of a half-bridge piezoresistive accelerometer. The accelerometer of the transducer 402 includes a complementary pair of piezoresistive elements $R_1$ 410 and $R_2$ 412. The half bridge forms a Y configuration in which the apex of the Y is connected in series with a diode 414 to the conductor 210 through the resistor $R_s$ 408. The piezoresistive element $R_1$ 410 in one leg of the Y configuration is connected directly to the conductor 208. The piezoresistive element $R_2$ 412 in the other leg of the Y configuration is connected to the conductor 208 through a diode 416. The diodes 414 and 416 both conduct in the same direction when forward biased.

Similarly, the second transducing element 404 includes piezoresistive elements $R_3$ 418 and $R_4$ 420 in a Y configuration. The apex of the Y is coupled through a diode 422 to the conductor 210 through the resistor $R_s$ 408, and the piezoresistive element $R_3$ 418 is connected directly to the conductor 208. The other piezoresistive element $R_4$ 420 is coupled to the conductor 208 through a diode 424. When forward biased, the diodes 422 and 424 conduct in a direction opposite to that of the diodes 414 and 416.

As shown in FIG. 5, the excitation signal emitted by the power source 406 preferably is a triangle wave having a peak magnitude greater than $2V_f$, where $V_f$ is the forward bias voltage of each diode.

Using the following equations in Table 1, the resistance of each piezoresistive element can be measured independently over the two conductors 208 and 210:

TABLE 1

| PHASE | $V_{in}$ | DIODES SWITCHED ON | RESISTANCE MEASUREMENT |
|---|---|---|---|
| (1a) | $V_f \leq V_{in} < 2V_f$ | 414 | $R_1 = \dfrac{V_{in} - V_f}{I} - R_s$ |
| (1b) | $V_{in} \geq 2V_f$ | 414, 416 | $R_2 = \dfrac{R_1(V_{in} - R_s I - 2V_f)}{R_1 I - V_{in} + R_s I + V_f}$ |
| (2a) | $-2V_f < V_{in} \leq -V_f$ | 422 | $R_3 = \dfrac{V_{in} + V_f}{I} - R_s$ |
| (2b) | $V_{in} \leq -2V_f$ | 422, 424 | $R_4 = \dfrac{R_3(V_{in} - R_s I + 2V_f)}{R_3 I - V_{in} + R_s I - V_f}$ |

The half bridge configuration of FIG. 4 can achieve temperature compensation and provide double the output sensitivity of the sensor circuit of FIG. 3. The piezoresistive elements in each half bridge are mounted in a sensor such that accelerations have opposite effects on their resistance, e.g., a positive acceleration should increase the resistance of element $R_1$ 410 and decrease the resistance of element $R_2$ 412. The acceleration value is proportional to the difference of the resistance values of each half bridge, e.g., proportional to $R_1 - R_2$. Similar to the sensor of FIG. 3, because temperature will have the same effect on both resistances of each half bridge, e.g., $R_1$ 410 and $R_2$ 412, the temperature effects are canceled by subtracting the resistance values.

According to the equations of Table 1, during a phase 1a of the excitation signal $V_{in}$, the excitation voltage is greater than the forward bias voltage of the diodes, but less than twice that value. In this situation only the diode 414 is switched on while all other diodes do not conduct. Because current flows only through the piezoresistive element $R_1$ 410, the value of that resistance can be calculated during the first phase.

During phase 1b, the excitation voltage exceeds twice the forward bias voltage, thus causing diodes 416 and 414 to conduct current through piezoresistive elements $R_1$ 410 and $R_2$ 412. During this phase, because the resistance of $R_1$ 410 is already known from phase 1a, the resistance of $R_2$ 412 can be calculated. During phase 1a, the value of $R_1$ 410 can be stored in a memory device (not shown) for use during phase 1b to calculate $R_2$ 412. During phase 1b, the difference $(R_1 - R_2)$ can also be calculated. Using conventional techniques, a temperature-compensated acceleration value proportional to the differential resistance value can be calculated.

Similarly, when the excitation voltage swings to negative values during phases 2a and 2b, the values of the piezoresistive elements $R_3$ 418 and $R_4$ 420 and their difference can be calculated for the half bridge in transducer 404.

Note that because the resistance of $R_s$ 408 is negligible, the voltage drop across $R_s$ 408 can be ignored when determining the input voltage $V_{in}$ necessary to cause the diodes to conduct. For the same reason, $R_s$ can be removed from the equations of Table 1 without significantly affecting the transducer resistance measurement.

It should be understood that for both the sensor circuits of FIGS. 3 and 4, any excitation signal exhibiting similar characteristics may be employed. For example, any bipolar signal that swings between voltages exceeding positive and negative values of the forward bias voltage can be used for the circuit of FIG. 3. The sensor of FIG. 4 can be excited by a bipolar signal that swings between voltage magnitudes exceeding the $-2V_f$ to $+2V_f$ range, and that has a slope permitting time for measurements in the four voltage ranges of Table 1.

The frequency of the excitation signal need only be high enough to permit adequate sampling of the resistances so as to obtain an accurate representation of the accelerations experienced by each sensor. As described below, the sensors are used to measure cardiac wall motion or body movement. Based upon the typical accelerations exhibited by these parameters, a sampling frequency in the range of approximately 500 samples/second to 10 kilosamples/second for each piezoresistive element is more than sufficient. To obtain these rates, the excitation signal must operate in a frequency range of 1K-20K samples/second for the sensor of FIG. 3 (two resistor samples/cycle for a temperature-compensated sensor), and in a frequency range of 2K-40K for the sensor of FIG. 4 (four resistor samples for a temperature-compensated sensor). Although the second sensor circuit must run at twice the frequency as the first circuit, one should note that the circuit of FIG. 4 can measure independent accelerations in two directions while achieving temperature compensation, as described below. In contrast, the circuit of FIG. 3, when configured to compensate for temperature variations, can measure motion in only one independent direction.

Various mounting configurations of the sensors of the present invention will now be described. FIG. 6 illustrates a cantilever beam mount 600 for the multiplexed motion sensor of the present invention. Using the cantilever beam mount 600, a cardiac wall motion sensor of the present invention may be mounted in a pacemaker or cardiac monitor lead, wherein the lead is in contact with a cardiac wall. For example, the sensor may be mounted in the ring or the tip of an endocardial lead electrode. Alternatively, the sensor may be mounted in an epicardial patch electrode or a myocardial active-fixation lead (leads not shown). When used as a physical activity sensor, the sensor of the present invention may, for example, be mounted within the body of a pacemaker (not shown). Preferably, the sensor can be mounted onto a hybrid within the pacemaker. The hybrid supports circuitry which allows the pacemaker to provide rate-responsive pacing therapy to a patient. Detailed descriptions of the mounting of cardiac wall motion sensors and physical activity sensors may respectively be found in commonly-assigned, copending U.S. patent application Ser. Nos. 08/091,636, now U.S. Pat. No. 5,628,777 (described above), and U.S. Pat. No. 5,383,473, issued Jan. 24, 1995 entitled "Rate-Responsive Implantable Stimulation Device Having a Miniature Hybrid-Mountable Accelerometer-Based Sensor and Method of Fabrication," of Moberg.

For convenience, the mounting of an accelerometer, as taught in commonly-assigned U.S. patent application Ser. No. 08/091,636, filed Jul. 14, 1993, entitled "Implantable Leads Incorporating Cardiac Wall Motion Sensors and Method of Fabrication and a System and Method for Detecting Cardiac Arrhythmias using a Cardiac Wall Motion sensor Signal," is described briefly below, with corresponding elements renumbered using a "1000" series.

In FIG. 9, a preferred embodiment of a myocardial active-fixation lead incorporating a cardiac wall motion sensor in accordance with the principles of the present invention is described. A myocardial active-fixation lead 1090 includes a screw-in electrode 1092 mounted at the distal end of the myocardial active-fixation lead 1090 in an electrode mount 1094. The electrode mount 1094 is disposed within an electrically insulating, substantially inflexible carrier 1096. The electrode 1092, which is shown as a helical barb in FIG. 9, is intended to be screwed into myocardial tissue (not shown) when a cardiac stimulating device (not shown) is implanted. The electrode 1092 typically serves as one pole in the delivery of therapeutic electrical stimulation, and is typically used in conjunction with a unipolar endocardial lead (not shown), or an epicardial patch electrode (not shown), which serves as the opposite poles In accordance with the invention, a cardiac wall motion sensor 1468 is adhered to the electrode mount 1094 with a biocompatible epoxy or silicone. The cardiac wall motion sensor 1468 provides a signal indicative of motion of a region of the cardiac wall (not shown) to which the carrier 1096 is attached. The cardiac wall motion sensor 1468 is connectable to the implantable cardiac stimulating device by two wires 1098 and 1100, which are disposed within an insulated cable 1102. Also disposed within the insulated cable 1102 is a wire 1104, which serves to connect the electrode 1092 to the cardiac stimulating device.

The embodiment shown in FIG. 9 uses a bifurcated connector including two connectors 1106 and 1108 and two branches 1110 and 1112 (although a tripolar in-line terminal is also possible). Also, a two-wire configuration is also possible, in which the wire 1104 is shared by the electrode 1092 and the cardiac wall motion sensor 1468.

The shape of the electrode 1092 may be selected to be any shape known to effectively penetrate the cardiac wall such that the electrode 1092 is in contact with and secured to myocardial tissue. For example, the electrode 1092 may alternatively be shaped as a spear.

As shown in FIG. 10, a preferred embodiment of an endocardial lead incorporating a cardiac wall motion sensor in accordance with the principles of the present invention is described. In this embodiment, a lead body 1114 of an endocardial lead 1116 is preferably a flexible, multi-lumen catheter made substantially from silicone rubber. As described in greater detail below, the lead body 1114 serves as a carrier for delivering a cardiac wall motion sensor 1568 to a region of the cardiac wall (not shown).

Extending from the distal end of the endocardial lead 1116 is a helically-shaped tip electrode 1118 which is connected to an electrode mount 1120. Before the tip electrode 1118 is secured to a region of the cardiac wall, the tip electrode 1118 is substantially disposed within a screw housing 1122. The tip electrode 1118 is intended to be secured to myocardial tissue (not shown) of either the right atrium or the right ventricle.

A stylet 1124 is used to facilitate securing the tip electrode 1118 into myocardial tissue. The stylet 1124 extends from the proximal end of the endocardial lead 1116 to the tip electrode 1118, and is disposed within a helically wound wire 1126 within the lead body 1114. The stylet 1124 is typically removed from the endocardial lead 1116 after the tip electrode 1118 has been secured.

The endocardial lead 1116 further includes a ring electrode 1130. The ring electrode 1130 is an electrically conductive cylinder, preferably made from a platinum/iridium alloy (with a typical platinum to iridium composition ratio of about 90/10 or about 80/20), that has an exposed external surface. The ring electrode 1130 is connectable to an implantable cardiac stimulating device (not shown) by a wire 1132 connected to a terminal 1134 of a bifurcated, unipolar/tripolar in-line connector 1136 (although other connectors may be used, such as a quadrapolar in-line connector). When the implantable cardiac stimulating device is used to provide pacing therapy, the tip electrode 1118 typically serves as the cathode and the ring electrode 1130 typically serves as the anode. In addition, cardiac electrical activity can be sensed between the tip electrode 1118 and the ring electrode 1130.

The lower portion of the ring electrode 1130, as shown in FIG. 10, provides a passageway for the wire 1126 and the stylet 1124 disposed therein. The upper portion of the ring electrode 1130 houses the cardiac wall motion sensor 1568 (shown schematically in FIG. 10, and described in greater detail below). The cardiac wall motion sensor 1568 provides a signal indicative of motion of a region of the cardiac wall (not shown) to which the endocardial lead 1116 is affixed. A wire 1138, which is connected to the cardiac wall motion sensor 1568 by a feedthrough terminal 1140 within a feedthrough 1142, is used to electrically connect the cardiac wall motion sensor 1568 to the implantable cardiac stimulating device. The cardiac wall motion sensor 1568 is also connected to the ring electrode 1130 by a wire 1144 which provides a return line for the cardiac wall motion sensor 1568. Such a configuration permits the endocardial lead 1116 to be manufactured as a four-wire lead. But, as previously described, the cardiac wall motion sensor 1568 should include electronics (not shown) to insulate the cardiac wall motion sensor 1568 from stimulation pulses. Alternatively, a wire (not shown) may be provided to supply the cardiac wall motion sensor 1568 with a dedicated return line, in which case, the endocardial lead 1116 would contain five wires.

The endocardial lead 1116 preferably further includes a shocking coil 1146 for delivering high energy defibrillation shocks or low energy cardioversion shocks. The shocking coil 1146 is electrically connectable to the implantable cardiac stimulating device by a wire 1148 which is typically connected to a crimp tube (not shown) that is welded to a shocking coil termination ring 1150. The wire 1148 is connectable to the implantable cardiac stimulating device by a unipolar terminal 1152 of the bifurcated connector 1136. Typically, the shocking coil 1146 is used in combination with an epicardial or subcutaneous patch electrode (not shown), or a second endocardial lead (not shown), or some combination, for delivering therapeutic shocks. Alternatively, the endocardial lead 1116 may include a second shocking coil (not shown) positioned so that a defibrillation or cardioversion shock can be delivered between two coils on the same endocardial lead. Even further, an endocardial lead including two shocking coils, or two endocardial leads each including a single shocking coil, may be used in combination with an epicardial or subcutaneous patch electrode, to provide multiple current pathways and polarity selection for therapeutic shocks.

The wire 1126 is used to electrically connect the tip electrode 1118 to the implantable cardiac stimulating device. This is accomplished by removing the stylet 1124 after the tip electrode 1118 is secured, and inserting the bifurcated connector 1136 of the endocardial lead 1116 into a connector (not shown) in the implantable cardiac stimulation device, thereby electrically connecting the wires 1126, 1132, 1138 and 1148 to the pulse generating electronics (not shown) within the implantable cardiac stimulating device.

Figure 11:
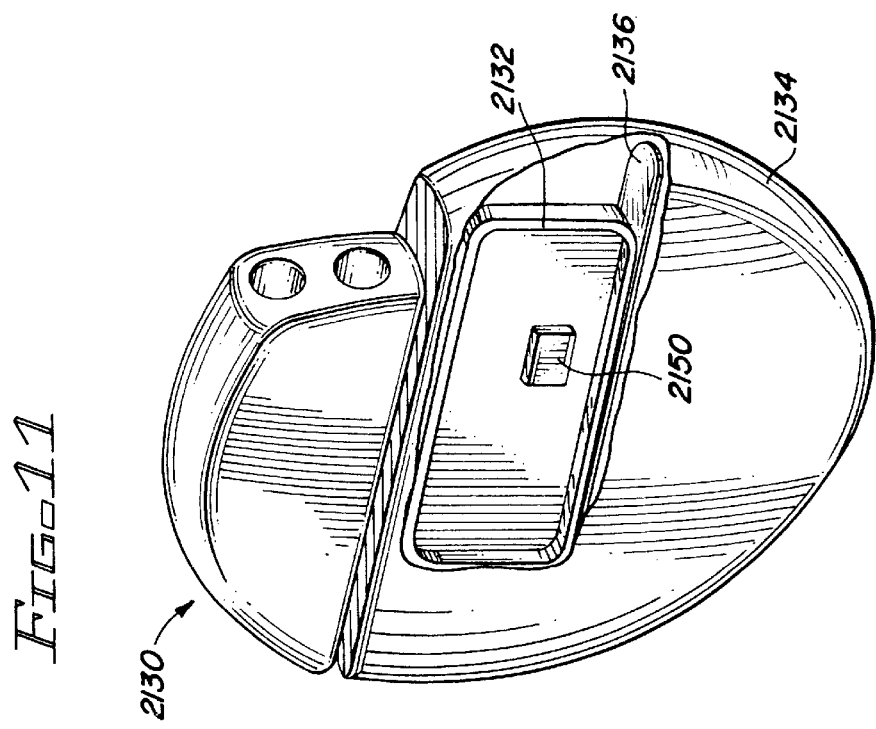
FIG. 11 is a partial cutaway view of a rate-responsive implantable stimulation device having a physical activity sensor mounted to a hybrid in accordance with the principles of the present invention.

In FIG. 11, a portion of the interior of a pacemaker is shown to illustrate a preferred mounting location for a physical activity sensor in accordance with the principles of the present invention. In FIG. 11, a pacemaker 2130 is shown having a hybrid 2132 disposed within an implantable housing 2134. A battery 2136 is disposed within the lower portion of the implantable housing 2134. The pacemaker 2130 may include other components, but they are not pertinent in the present context.

The hybrid 2132 supports circuitry (not shown) which allows the pacemaker to provide rate-responsive pacing therapy to a patient (not shown). In this preferred embodiment, a sensor 2150 (schematically depicted as a block in FIG. 11 and not drawn to scale) is bonded to a surface of the hybrid 2132, as is known in the art. The hybrid 2132 has conductive traces deposited thereon (not shown) and the sensor 2150 has first and second electrical contacts (not shown) which contact the conductive traces (the connections are hidden from view in FIG. 11). Mounting the sensor 2150 to the hybrid 2132 is advantageous, because assembly and installation of the sensor 2150 may be incorporated into the fabrication process of the hybrid 2132.

Figure 12:
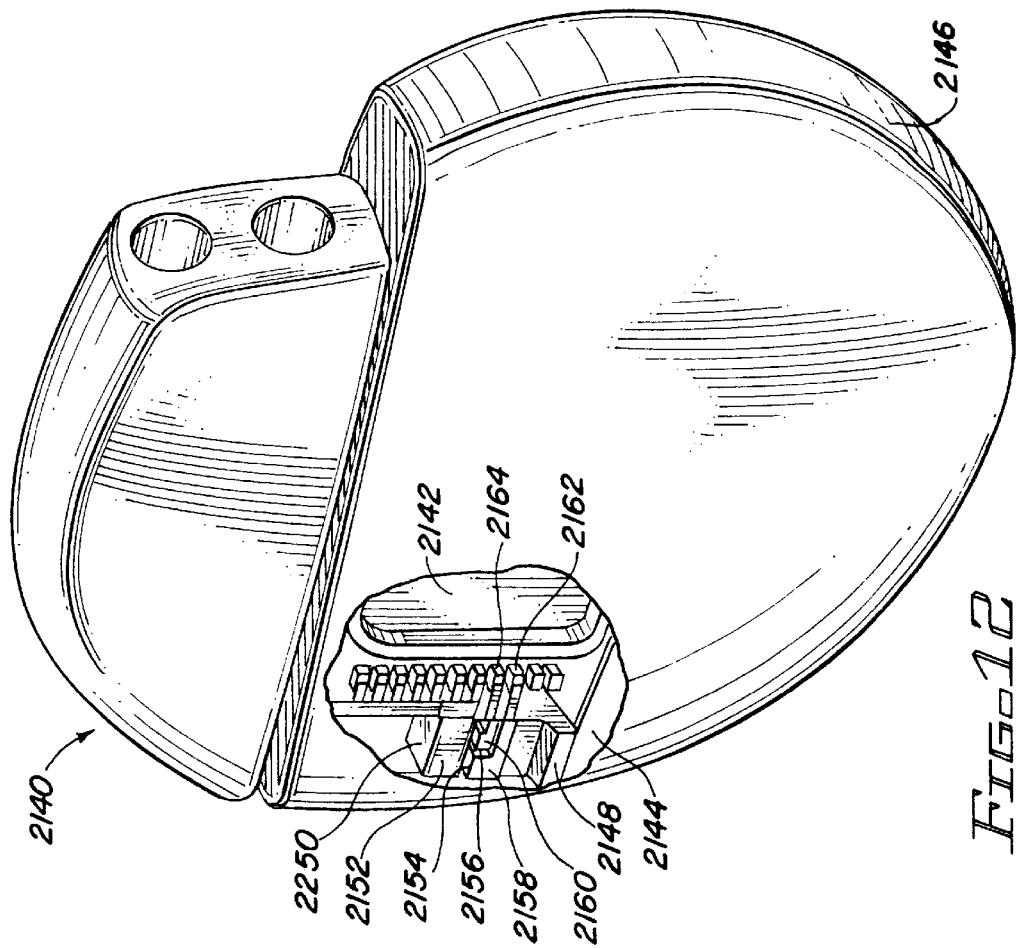
FIG. 12 is a partial cutaway view of a rate-responsive implantable stimulation device having the physical activity sensor disposed within a battery support in accordance with the principles of the present invention.

An alternative mounting location for the physical activity sensor of the present invention is shown in FIG. 12. To illustrate this embodiment, a pacemaker 2140 is shown having a hybrid 2142 and a battery 2144 disposed within an implantable housing 2146. The pacemaker 2140 also includes a battery support 2148 which is adhered to the interior of the pacemaker 2140 and serves to secure the battery 2144.

The battery support 2148 includes a cavity which contains a sensor 2250. A substrate 2152, upon which the sensor 2250 is mounted, has two electrically conductive conduits (not shown) for electrically connecting first and second supports (not shown), to a pair of conductive pads 2154 and 2156 adhered to the exterior surface of the substrate 2152. A pair of wires 2158 and 2160 are used to connect the conductive pads 2154 and 2156 to a pair of terminals 2162 and 2164 on the hybrid 2142. Circuitry (not shown) on the hybrid 2142 is thereby provided with the output signal from the sensor 2250, which may be subsequently processed and used by the pacemaker 2140 to provide rate-responsive pacing therapy.

A substrate 602 of the cantilever mount 600 serves as a base member to be mounted to an implantable lead or to an implantable medical device housing. Local electronics 604 are mounted to the substrate 602. The local electronics include, for example, the diodes of the motion sensors of FIGS. 3 and 4. Conductors 208 and 210 exit the local electronics 604 to provide current measurements indicative of sensor motion to signal processing circuitry in the implantable medical device (not shown).

A cantilever beam 606 is affixed to the substrate 602. A vertical support 608 may be used to affix the cantilever beam 606 to the substrate 602. An offset mass 610 is affixed to the distal end of the cantilever beam 606. FIG. 6 illustrates the use of an offset mass 610, but one skilled in the art will recognize that, as an alternative, the beam mount 600 may employ a centered mass that is symmetrical about the planar surface of the cantilever beam 606.

A first piezoresistive material 612 is disposed on the top planar surface of the beam 606. Similarly, a second (preferably identical) piezoresistive material 614 is disposed on the bottom surface of the beam 606. When employed as a mount for the sensor of FIG. 3, the piezoresistive coatings 612 and 614 are the piezoresistive accelerometers 306 and 310, each disposed on an opposite surface so that the resistance of one coating increases while the resistance of the other decreases as the beam 606 is deflected. This configuration provides temperature compensation for the motion sensor 300.

Alternatively, the cantilever beam 606 may be coated on only one side, as shown in the cantilever beam mount 700 in FIG. 7. In that case, one piezoresistive accelerometer may be mounted on one beam, and another accelerometer mounted on another beam of a cantilever mount similar or identical to that of mount 600. The two cantilever mounts may then be mounted orthogonal to each other and use symmetric masses to provide motion measurements in distinct orthogonal directions over only two conductors 208 and 210. The disadvantage to this arrangement is that the acceleration measurements are not temperature compensated.

As another alternative, the present invention may include two cantilever mounts, using the cantilever beam mount 800 shown in FIG. 8, in which the piezoresistive coatings 812, 814 on opposite sides of the beam of the first mount are the complementary pair of elements R1 410 and R2 412, while the piezoresistive coatings 812, 814 on the second mount are the complementary pair of piezoresistive elements R3 418 and R4 420. Again, the cantilever mounts in this embodiment preferably employ symmetric masses and are disposed perpendicular to each other to provide motion measurements in individual orthogonal directions. The advantage of using the motion sensor 400 over the motion sensor 300 is that the sensor 400 can provide orthogonal measurements that are temperature compensated over the two conductors 208 and 210, while the sensor 300 can not provide temperature-compensated orthogonal measurements using only two wires.

Through the use of multiplexing, the present invention provides motion sensors that use fewer conductors than their conventional counterparts. For example, for two-axis measurements that are not temperature-compensated, the motion sensor 300 requires only two wires, while comparable conventional sensors require three wires (two wires per sensor with one in common). For temperature-compensated two-axis measurements, the sensor 400 uses only two measurement wires, while comparable conventional sensors require five wires (three for each sensor with one wire in common). Accordingly, the sensors of the present invention conserve valuable space within implantable medical devices that are used to measure cardiac motion or physical activity.

It will be appreciated that various modifications and alterations might be made by those skilled in the art without departing from the spirit and scope of the present invention. The invention should, therefore, be measured in terms of the claims which follow.

What is claimed is:

1. A two-conductor multiplexed motion sensor for use with an implantable medical device, wherein the implantable medical device includes circuitry for monitoring or stimulating cardiac activity, the sensor comprising:

a first conductor;

a second conductor;

a first transducing circuit for providing a first motion measurement indicative of sensor acceleration during a first phase, wherein the first transducing circuit provides the first motion measurement to the implantable medical device over the first and second conductors; and a second transducing circuit for providing a second motion measurement indicative of sensor acceleration during a second phase, wherein the second transducing circuit is connected in parallel to the first transducing circuit so as to provide the second motion measurement to the implantable medical device over the first and second conductors, wherein the first and second phases are nonoverlapping periods of time.

2. The sensor of claim 1, wherein the sensor is a cardiac wall motion sensor.

3. The sensor of claim 2, wherein the sensor is mounted in a lead of the implantable medical device, the lead being in contact with a cardiac wall.

4. The sensor of claim 2, wherein the first and second transducer circuits are positioned noncoaxially so that the sensor is sensitive to cardiac wall acceleration along a plurality of axes.

5. The sensor of claim 1, wherein the sensor is a physical activity sensor.

6. The sensor of claim 5, wherein the physical activity sensor is mounted to the implantable medical device to detect acceleration of a body in which the device is implanted.

7. The sensor of claim 6, wherein the first and second transducer circuits are positioned orthogonally so that the physical activity sensor is a multi-axial sensor for detecting up-down body acceleration along a vertical axis and left-right body acceleration along a lateral axis.

8. The sensor of claim 1, wherein:
over the first and second conductors, the first and second transducing circuits receive an excitation signal having a first polarity during the first phase and a second polarity opposite the first polarity during the second phase;
in response to the excitation signal being in the first polarity, the first transducing circuit conducts in a first direction and the second transducing circuit does not conduct;
in response to the excitation signal being in the second polarity, the second transducing circuit conducts in a second direction opposite the first direction and the first transducing circuit does not conduct; and
the first and second motion measurements are respectively provided to the implantable medical device when the first and second transducing circuits conduct.

9. The sensor of claim 8, wherein:
the first transducing circuit includes a first piezoresistive material in series with a first diode, and the first diode is positioned to conduct in the first direction during the first phase;
the second transducing circuit includes a second piezoresistive material in series with a second diode, and the second diode is positioned to conduct in the second direction during the second phase;
the piezoresistive materials vary their respective resistances in response to sensor acceleration;
the first motion measurement is the resistance of the first piezoresistive material determined when the first transducing circuit conducts, and the second motion measurement is the resistance of the second piezoresistive material determined when the second transducing circuit conducts.

10. The sensor of claim 8, each transducing circuit comprising a piezoresistive half bridge, each half bridge including:
a first leg having a first piezoresistive material;
a second leg having a second piezoresistive material, wherein
the piezoresistive materials vary their respective resistances in response to sensor acceleration;
the first leg conducts when a voltage magnitude of the excitation signal exceeds a first voltage magnitude level to thereby permit the resistance of the first piezoresistive material to be determined,
the first and second legs conduct when the voltage magnitude of the excitation signal exceeds a second voltage magnitude level greater than the first voltage magnitude level to thereby permit the resistance of the second piezoresistive material to be determined;
the first motion measurement is the difference in the resistances of the first and second piezoresistive materials in the first transducing circuit determined when the first transducing circuit conducts, and
the second motion measurement is the difference in the resistances of the first and second piezoresistive materials in the second transducing circuit determined when the second transducing circuit conducts.

11. A two-conductor multiplexed motion sensor for use with an implantable medical device, wherein the implantable medical device includes circuitry for monitoring or stimulating cardiac activity, the sensor comprising:
a first conductor;
a second conductor;
a first transducing circuit including transducing material having an electrical characteristic that varies measurably when the material is subjected to mechanical stress, the first transducing circuit for providing a first motion measurement indicative of sensor acceleration during a first phase, wherein the first transducing circuit provides the first motion measurement to the implantable medical device over the first and second conductors;
a second transducing circuit including the transducing material for providing a second motion measurement indicative of sensor acceleration during a second phase, wherein the second transducing circuit is connected in parallel to the first transducing circuit so as to provide the second motion measurement to the implantable medical device over the first and second conductors, wherein the first and second phases are nonoverlapping periods of time;
at least one base member;
at least one mass;
at least one cantilever beam having a fixed end that is fixed to a corresponding base member, and a free end upon which is disposed a corresponding mass, wherein the transducing material is disposed on the at least one beam for providing a beam measurement indicative of acceleration experienced by the beam as the beam deflects.

12. The sensor of claim 11, wherein:
a first cantilever beam is positioned noncoaxially with respect to a second cantilever beam so that the corresponding beam measurements are respectively the first and second motion measurements and are indicative of sensor acceleration along a plurality of axes.

13. The sensor of claim 12, wherein a first mass is symmetrically disposed about a planar surface of the first beam and a second mass is symmetrically disposed about a planar surface of the second beam, so that the first transducing circuit is sensitive to acceleration along a first axis perpendicular to the planar surface of the first beam and the second transducing circuit is sensitive to acceleration along a second axis perpendicular to the planar surface of the second beam, and the first and second axes are orthogonal so that the first and second motion measurements are respectively indicative of acceleration along the first and second axes.

14. The sensor of claim 12, wherein a first mass is asymmetrically disposed about a planar surface of the first beam and a second mass is asymmetrically disposed about a planar surface of the second beam, so that the first transducing circuit is sensitive to acceleration along axes perpendicular to and coaxial with the planar surface of the first beam and the second transducing circuit is sensitive to acceleration along axes perpendicular to and coaxial with the planar surface of the second beam, and the first and second beams are positioned with respect to each other so that the first and second motion measurements are together indicative of acceleration along three orthogonal axes.

15. The sensor of claim 11, wherein:

over the first and second conductors, the first and second transducing circuits receive an excitation signal having a first polarity during the first phase and a second polarity opposite the first polarity during the second phase;

in response to the excitation signal being in the first polarity, the first transducing circuit conducts in a first direction and the second transducing circuit does not conduct;

in response to the excitation signal being in the second polarity, the second transducing circuit conducts in a second direction opposite the first direction and the first transducing circuit does not conduct; and the first and second motion measurements are provided to the implantable medical device when the respective first and second transducing circuits conduct.

16. The sensor of claim 15, the transducing material comprising a first piezoresistive material and a second piezoresistive material disposed on opposite planar surfaces of a first beam, wherein:

the first transducing circuit includes the first piezoresistive material in series with a first diode, and the first diode is positioned to conduct in the first direction during the first phase;

the second transducing circuit includes the second piezoresistive material in series with a second diode, and the second diode is positioned to conduct in the second direction during the second phase;

the piezoresistive materials vary their respective resistances in response to sensor acceleration; and the first motion measurement is the resistance of the first piezoresistive material determined when the first transducing circuit conducts, and the second motion measurement is the resistance of the second piezoresistive material determined when the second transducing circuit conducts, the difference in the first and second motion measurements providing a temperature-compensated motion measurement to the implantable medical device.

17. The sensor of claim 15, the transducing material comprising a first piezoresistive material disposed on a planar surface of a first beam and a second piezoresistive material disposed on a planar surface of a second beam, wherein the first transducing circuit includes the first piezoresistive material in series with a first diode, and the first diode is positioned to conduct in the first direction during the first phase;

the second transducing circuit includes the second piezoresistive material in series with a second diode, and the second diode is positioned to conduct in the second direction during the second phase;

the piezoresistive materials vary their respective resistances in response to sensor acceleration; and the first motion measurement is the resistance of the first piezoresistive material determined when the first transducing circuit conducts, and the second motion measurement is the resistance of the second piezoresistive material determined when the second transducing circuit conducts.

18. The sensor of claim 15, the transducing material comprising piezoresistive material that varies its resistance in response to sensor acceleration, each transducing circuit comprising a piezoresistive half bridge, each half bridge including:

a first leg having a first piezoresistive material disposed on a first planar surface of a corresponding cantilever beam;

a second leg having a second piezoresistive material disposed on a second planar surface opposite the first planar surface of the corresponding cantilever beam, wherein the first leg conducts when a voltage magnitude of the excitation signal exceeds a first voltage magnitude level to thereby permit the resistance of the first piezoresistive material to be determined, the first and second legs conduct when the voltage magnitude of the excitation signal exceeds a second voltage magnitude level greater than the first voltage magnitude level to thereby permit the resistance of the second piezoresistive material to be determined, the first motion measurement is the difference in the resistances of the first and second piezoresistive materials in the first transducing circuit determined when the first transducing circuit conducts, and the second motion measurement is the difference in the resistances of the first and second piezoresistive materials in the second transducing circuit determined when the second transducing circuit conducts, whereby the first and second motion measurements are each temperature-compensated motion measurements provided to the implantable medical device.

19. In an implantable medical device including a motion sensor and circuitry for monitoring or stimulating cardiac activity, a method for providing motion measurements from the sensor to the implantable medical device, the method comprising:

providing a first motion measurement indicative of sensor acceleration to the implantable medical device during a first phase, wherein the first motion measurement is provided over first and second conductors from a first transducing circuit in the sensor;

providing a second motion measurement indicative of sensor acceleration to the implantable medical device during a second phase, wherein the second motion measurement is provided over the first and second conductors from a second transducing circuit in the sensor, the second transducing circuit being connected in parallel to the first transducing circuit, wherein the first and second phases are nonoverlapping periods of time.

20. The method of claim 19 further comprising the steps of:

over the first and second conductors, exciting the first and second transducing circuits with an excitation signal having a first polarity during the first phase and a second polarity opposite the first polarity during the second phase;

in response to the excitation signal being in the first polarity, the first transducing circuit conducting in a first direction and the second transducing circuit not conducting; and in response to the excitation signal being in the second polarity, the second transducing circuit conducting in a second direction opposite the first direction and the first transducing circuit not conducting, wherein the first and second motion measurements are respectively provided to the implantable medical device when the first and second transducing circuits conduct.

21. The method of claim 20, wherein:

the first transducing circuit includes a first piezoresistive material in series with a first diode, and the first diode is positioned to conduct in the first direction during the first phase;

the second transducing circuit includes a second piezoresistive material in series with a second diode, and the second diode is positioned to conduct in the second direction during the second phase;

the piezoresistive materials vary their respective resistances in response to sensor acceleration;

the method further comprising the steps of:
determining the resistance of the first piezoresistive material when the first transducing circuit conducts, wherein the resistance determined during the first phase is the first motion measurement; and
determining the resistance of the second piezoresistive material when the second transducing circuit conducts, wherein the resistance determined during the second phase is the second motion measurement.

22. The method of claim 20, each transducing circuit comprising a piezoresistive half bridge, each half bridge including:

a first leg having a first piezoresistive material;

a second leg having a second piezoresistive material, wherein the first leg conducts when a voltage magnitude of the excitation signal exceeds a first voltage magnitude level to thereby permit the resistance of the first piezoresistive material to be determined, the first and second legs conduct when the voltage magnitude of the excitation signal exceeds a second voltage magnitude level greater than the first voltage magnitude level to thereby permit the resistance of the second piezoresistive material to be determined, wherein the piezoresistive materials vary their respective resistances in response to sensor acceleration;

the method further comprising the steps of:

determining the difference in the resistances of the first and second piezoresistive materials in the first transducing circuit when the first transducing circuit conducts, wherein the difference determined during the first phase is the first motion measurement, and determining the difference in the resistances of the first and second piezoresistive materials in the second transducing circuit when the second transducing circuit conducts, wherein the difference determined during the second phase is the second motion measurement.

23. The method of claim 20, wherein each transducing circuit further comprises a transducing material having an electrical characteristic that varies measurably when the material is subjected to mechanical stress; and the sensor further comprises:
at least one base member;
at least one mass;
at least one cantilever beam having a fixed end that is fixed to a corresponding base member, and a free end upon which is disposed a corresponding mass, wherein the transducing material is disposed on the at least one beam for providing a beam measurement indicative of acceleration experienced by the beam as the beam deflects.

24. The method of claim 23, the transducing material comprising a first piezoresistive material and a second piezoresistive material disposed on opposite planar surfaces of a first beam, wherein:

the first transducing circuit includes the first piezoresistive material in series with a first diode, and the first diode is positioned to conduct in the first direction during the first phase;

the second transducing circuit includes the second piezoresistive material in series with a second diode, and the second diode is positioned to conduct in the second direction during the second phase;

the piezoresistive materials vary their respective resistances in response to sensor acceleration;

the method further comprising the steps of:
determining the resistance of the first piezoresistive material when the first transducing circuit conducts;
determining the resistance of the second piezoresistive material when the second transducing circuit conducts; and
subtracting the resistance of the second piezoresistive material from the resistance of the first piezoresistive material to thereby provide a temperature-compensated motion measurement to the implantable medical device.

25. The method of claim 23, the transducing material comprising a first piezoresistive material disposed on a planar surface of a first beam and a second piezoresistive material disposed on a planar surface of a second beam, wherein:

the first transducing circuit includes the first piezoresistive material in series with a first diode, and the first diode is positioned to conduct in the first direction during the first phase;

the second transducing circuit includes the second piezoresistive material in series with a second diode, and the second diode is positioned to conduct in the second direction during the second phase;

the piezoresistive materials vary their respective resistances in response to sensor acceleration;

the method further comprising the steps of:
determining the resistance of the first piezoresistive material when the first transducing circuit conducts, wherein the resistance determined during the first phase is the first motion measurement; and
determining the resistance of the second piezoresistive material when the second transducing circuit conducts, wherein the resistance determined during the second phase is the second motion measurement.

26. The method of claim 23, the transducing material comprising piezoresistive material that varies its resistance in response to sensor acceleration, each transducing circuit comprising a piezoresistive half bridge, each half bridge including:

a first leg having a first piezoresistive material;

a second leg having a second piezoresistive material, wherein the first leg conducts when a voltage magnitude of the excitation signal exceeds a first voltage magnitude level to thereby permit the resistance of the first piezoresistive material to be determined, the first and second legs conduct when the voltage magnitude of the excitation signal exceeds a second voltage magnitude level greater than the first voltage magnitude level to thereby permit the resistance of the second piezoresistive material to be determined, the method further comprising the steps of:

determining the difference in the resistances of the first and second piezoresistive materials in the first transducing circuit when the first transducing circuit conducts, wherein the difference determined during the first phase is the first motion measurement, and determining the difference in the resistances of the first and second piezoresistive materials in the second transducing circuit when the second transducing circuit conducts, wherein the difference determined during the second phase is the second motion measurement, whereby the first and second motion measurements are each temperature-compensated motion measurements provided to the implantable medical device.

* * * * *